United States Patent [19]

Dandolu

[11] Patent Number: 5,588,952

[45] Date of Patent: Dec. 31, 1996

[54] INTRACARDIAC ILLUMINATOR WITH SUCTION

[76] Inventor: Bhaktavathsala R. Dandolu, 585 General Patterson Dr., Philadelphia, Pa. 19038

[21] Appl. No.: 101,452

[22] Filed: Aug. 2, 1993

[51] Int. Cl.[6] .................... A61B 1/06; A61M 1/00
[52] U.S. Cl. .................... 600/249; 604/902; 604/27; 606/2; 362/32
[58] Field of Search .................... 128/4 A, DIG. 21, 128/23, 22, 4, 6, 7; 606/1, 20, 4, 159, 160–162, 15; 433/29, 31, 96, 91; 604/35, 902, 264, 289, 294, 313; 600/249, 182, 170, 171; 362/32

[56] References Cited

U.S. PATENT DOCUMENTS

| | | | |
|---|---|---|---|
| 2,255,657 | 9/1941 | Freedman | 600/249 |
| 2,764,148 | 9/1956 | Sheldon | 128/4 |
| 3,089,484 | 5/1963 | Hett | 128/6 |
| 3,131,690 | 5/1964 | Innis et al. | 600/182 |
| 3,626,471 | 12/1971 | Florin . | |
| 3,699,950 | 10/1972 | Humphrey, Jr. et al. | 128/23 |
| 3,924,608 | 12/1975 | Mitsui | 128/6 |
| 4,175,545 | 11/1979 | Termanini | 128/6 X |
| 4,204,328 | 5/1980 | Kutner | 433/29 |
| 4,248,214 | 2/1981 | Hannah et al. | 128/23 X |
| 4,567,882 | 2/1986 | Heller | 600/249 |
| 4,583,528 | 4/1986 | Bauman | 128/11 |
| 4,617,013 | 10/1986 | Betz . | |
| 4,648,838 | 3/1987 | Schlachter | 433/29 |
| 4,662,871 | 5/1987 | Rafelson | 128/4 X |
| 4,759,347 | 7/1988 | Ando | 128/6 |
| 4,759,349 | 7/1988 | Betz et al. | 128/6 |
| 4,770,653 | 9/1988 | Shturman | 128/6 X |
| 4,773,396 | 9/1988 | Okazaki | 128/6 |
| 4,800,870 | 1/1989 | Reid, Jr. | 128/6 |
| 4,850,342 | 7/1989 | Hashiguchi et al. | 128/6 |
| 4,959,058 | 9/1990 | Michelson | 128/4 X |
| 5,213,092 | 5/1993 | Uram | 128/4 |
| 5,275,593 | 1/1994 | Easley et al. | 128/6 X |
| 5,281,134 | 1/1994 | Schulz | 433/29 |

FOREIGN PATENT DOCUMENTS 3939859  6/1991  Germany .................... 433/91

Primary Examiner—Richard J. Apley
Assistant Examiner—John P. Leubecker
Attorney, Agent, or Firm—Woodcock Washburn Kurtz Mackiewicz & Norris

[57] ABSTRACT

A thin flexible probe that combines illumination and aspiration includes a rigid, two-section housing for accommodating a flexible fiber optic cable and a flexible aspiration conduit. The fiber optic cable terminates at a distal end in an angle of less than 90 degrees relative to its longitudinal dimension so as to emit light in a radial direction through a transparent cover, which forms part of the first section of the housing. The aspiration conduit is connected in fluid communication with an aspiration tip, which forms part of the second section of the housing. A flexible tubular body surrounds the fiber optic cable and aspiration conduit and is sealed to the housing.

16 Claims, 3 Drawing Sheets

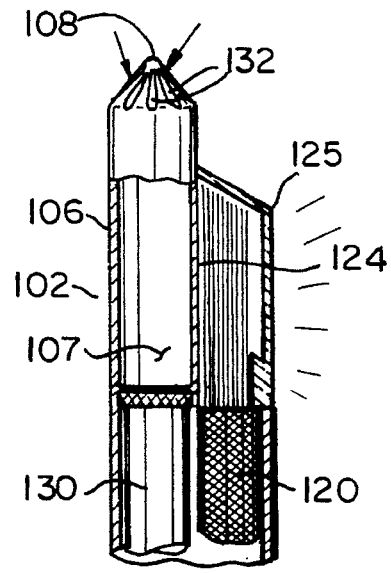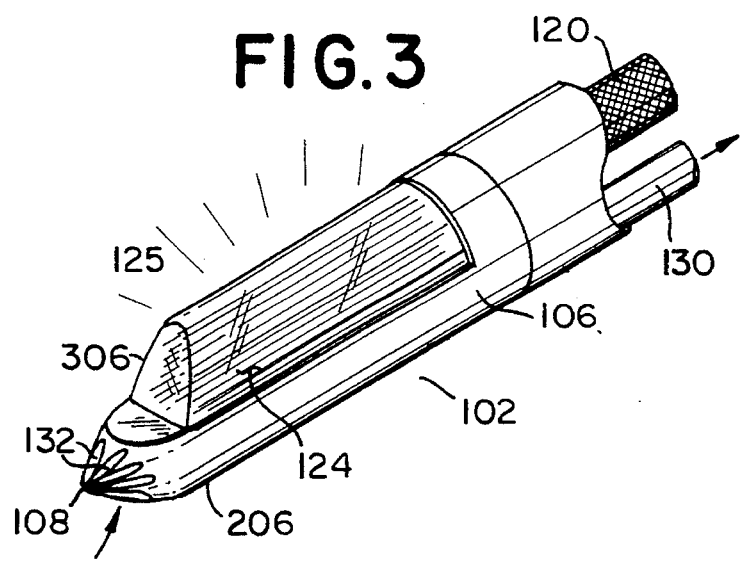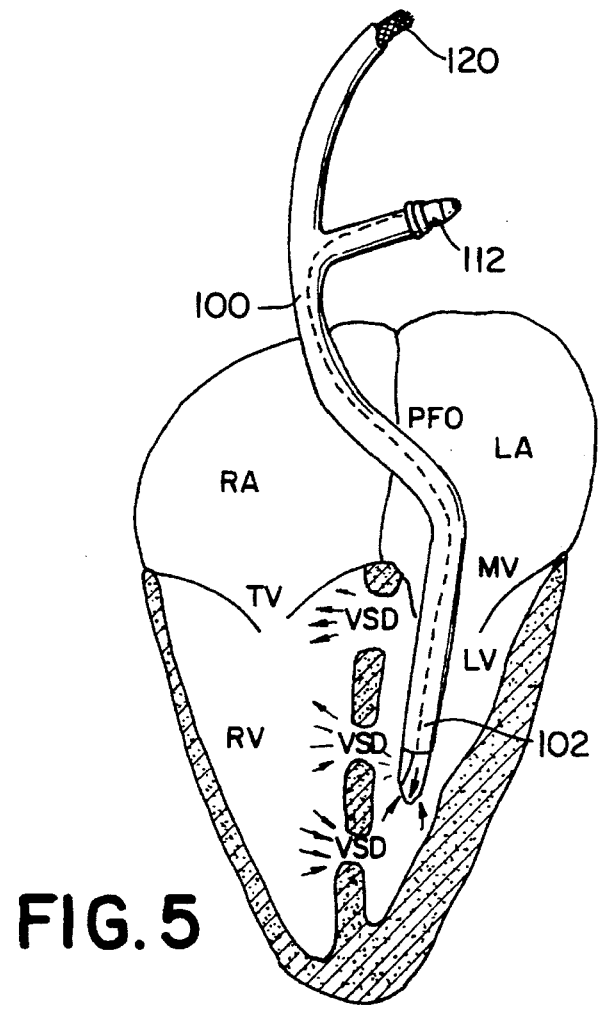

INTRACARDIAC ILLUMINATOR WITH SUCTION

The present application relates to surgical devices used to illuminate and aspirate the surgical field and, more particularly, to such devices that are adapted for intracardiac surgery or other procedures performed within body cavities.

BACKGROUND OF THE INVENTION

During surgery for the repair of congenital heart defects, especially the repair of a ventricular septal defect (VSD), Tetralogy of Fallot, and acquired heart defects, there is a need for good illumination inside the heart to facilitate accurate repair of the defects. Cardiac surgeons usually use headlights for this purpose. However, since these defects are situated deeply inside the heart and light cannot bend, headlights usually do not provide satisfactory illumination of the defect. The success of surgery for these heart defects depends on accurate and rapid repair, and good illumination is an important factor in ensuring successful surgery. Thus, there it would be highly desirable to provide an intracardiac device that will readily provide illumination of these types of defects.

The intracardiac procedures discussed above are examples of surgical procedures performed within body cavities and/or within organs. Any operation performed at such a site creates similar problems. First, of course, is the above-noted problem of there often being no direct illumination path to the surgical site. Headlights or light stands must be continually adjusted and manipulated to illuminate the field. Additionally, these sites constantly fill with blood and other body fluids, requiring frequent aspiration or else the site, even if properly illuminated, will be obscured. These considerations become acute in tight fields, an extreme example of which is within the chambers of the heart. It is difficult to insert and manipulate retractors, aspiration tips, surgical instruments and light probes all within the space available during open-heart surgery. Thus, it would be further desirable to provide a device that provided aspiration at an illuminated site while occupying a minimum amount of space.

Prior attempts to combine the illumination and aspiration functions have met with limited success. A rigid brain retractor that includes an illuminator and suction conduit is disclosed in U.S. Pat. No. 3,626,471—Florin. In the disclosed device, two tubular aspiration conduits are attached to the retractor and carry aspirated fluid away from the brain and a separate fiber optic probe is disposed alongside the exterior of the aspiration conduits and is also attached to the retractor. Aspirated fluid is drawn into a distal cross-sectional opening in each of the conduits.

Another device combining aspiration, irrigation and illumination into a coaxial probe is disclosed in U.S. Pat. No. 4,617,013—Betz. The irrigation tube is surrounded by the aspiration tube which, in turn, is surrounded by light emitting material. Thus, the area surrounding the specific aspiration or irrigation site is illuminated, but the central portion where the actual probe is disposed is not directly illuminated. The probe itself is of a relatively large cross-sectional area and is not flexible. The coaxial probe is brought into the area of interest manually by a surgeon or nurse holding the device. Aspiration fluid is drawn into the cross-sectional opening across the distal end of the device, in the same manner that irrigation fluid is introduced. The fiber optic portion of the coaxial probe is simply terminated at the same point as the aspiration and irrigation conduits.

Thus, the prior art has been unable to provide a device that permits clear and precise illumination of an interior surgical site while also aspirating blood and body fluids that had collected at the site. As noted above, it would be desirable that such a device occupy a minimum amount of space so as to not interfere with surgical procedures performed in tight fields, such as in intracardiac surgery. It is therefore a specific object of the present invention to provide illumination inside the heart during surgery for repair of intracardiac defects and, at the same time, clear the field of blood and fluids by aspirating the heart chamber in which it is placed.

SUMMARY OF THE INVENTION

The above described problems are solved and improved surgical procedures can be undertaken using apparatus made in accordance with the present invention. In a preferred embodiment, the present invention provides a flexible fiber optic cable, preferably having a diameter between 2–3 millimeters (0.08–0.12 inches), that is terminated within a housing at its distal end and an optical connector at its proximal end, a flexible aspiration conduit in fluid communication with an opening in the housing at its distal end and terminated by a connector at its proximal end. A flexible tubular body that overlies and seals the fiber optic cable and the aspiration conduit in a fluid tight manner.

Preferably, the housing comprises a reflector in optical communication with the fiber optic cable to diffuse and/or focus the light emitted; the reflector is most preferably an integral portion of the housing. The housing may also include a glass covering protecting the fiber optic cable. The housing preferably has an aspiration section having an aspiration opening for admitting fluid into the aspiration conduit and most preferably further includes at least one opening formed in a sidewall of the housing. In a preferred embodiment the fiber optic cable is longer than the aspiration conduit, and is most preferably about 180 cm (70.9 inches) long while the aspiration conduit is most preferably about 60 cm (23.6 inches) long. The diameter of the fiber optic cable and the aspiration conduit are both most preferably about 2–3 mm (0.08–0.12 inches). In the most preferred embodiment, the housing is comprised of stainless steel and the aspiration tubing and outer tubular body are comprised of silicone tubing.

Thus, the present invention discloses a flexible intracardiac illumination and cardiotomy suction/venting device for insertion within a heart. The probe has a flexible fiber optic cable with its proximal end terminated by an optical connector, and a flexible aspiration conduit with its proximal end terminated by a connector adapted to connect the aspiration conduit to a cardiotomy suction device. These are both joined to a housing adapted to connect to the distal end of the fiber optic cable that also provides an opening in fluid communication with the aspiration conduit. These components are all surrounded and sealed by a flexible tubular body.

The present invention also discloses improvements to methods of performing open heart surgery by permitting the step of introducing a single thin flexible probe comprising a fiber optic cable and an aspiration conduit into the interior of the heart. In one embodiment, this improved technique is used in a procedure to repair ventricular septal defects. In this case, the probe is inserted through an open right atrium, advanced through one of: a patent foramen ovale, an atrial septal defect or a slit formed in the interatrial septum. The probe is further advanced into the left atrium and across the mitral valve, into the left ventricle. Illumination from the left ventricle is transmitted through a ventricular septal defect, permitting its visualization.

BRIEF DESCRIPTION OF THE DRAWINGS

FIG. 3 is a perspective view of the distal end of an alternate embodiment of an intracardiac illuminator made in accordance with the present invention.

FIG. 4 is a cross-sectional side view of the alternate embodiment of the distal end of an intracardiac illuminator illustrated in FIG. 3.

FIG. 5 is a view of a heart showing the right and left ventricles laid open and an illuminator made in accordance with the present invention positioned in the left ventricle.

DETAILED DESCRIPTION OF THE PREFERRED EMBODIMENTS

Figure 1:
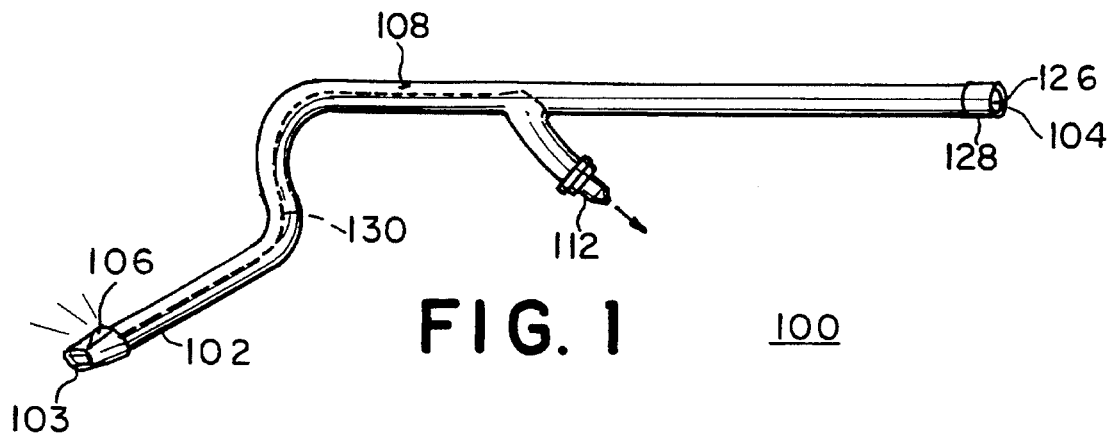
FIG. 1 is a perspective view of an intracardiac illuminator made in accordance with the present invention.

The present invention provides a fiber optic cable with an aspiration system that can be connected to a cardiotomy suction device during cardiopulmonary bypass. As seen in FIG. 1, the device 100 has two different ends, namely a cardiac end 102 and light source end 104. In a preferred embodiment, the device 100 measures about 180 cm (70.9 inches) in length from the cardiac end 102 to the light source end 104 and the fiber optic cable (not shown in FIG. 1) is continuous over the length of the device 100.

The distal tip 103 of the cardiac end 102 preferably includes a housing 106 that connects with a soft, pliable tubing 108 that preferably covers the rest of the device 100. The tubing 108 used in a preferred embodiment covers the entire device 100 making it fully autoclavable. In a preferred embodiment, the housing 106 is comprised of stainless steel and the tubing 108 is comprised of medical grade silicone. The housing 106 preferably tapers slightly from its base towards the distal tip 103, and is preferably fabricated to be free of sharp edges to make it atraumatic to tissue.

As shown in phantom in FIG. 1, the device 100 of the present invention includes an aspiration tube 130 that is disposed adjacent the fiber optic cable (not visible in this view) and which is also covered by the tubing 108. However, in the preferred embodiment shown, the aspiration tube does not run the full length of the device 100 and instead emerges from the tubing 108 and is terminated by a connector 112 as shown. Most preferably, the distance from the cardiac end 102 to the point where the aspiration tube exits the outer tubing 108 is about 60 cm (23.6 inches).

Figure 2:
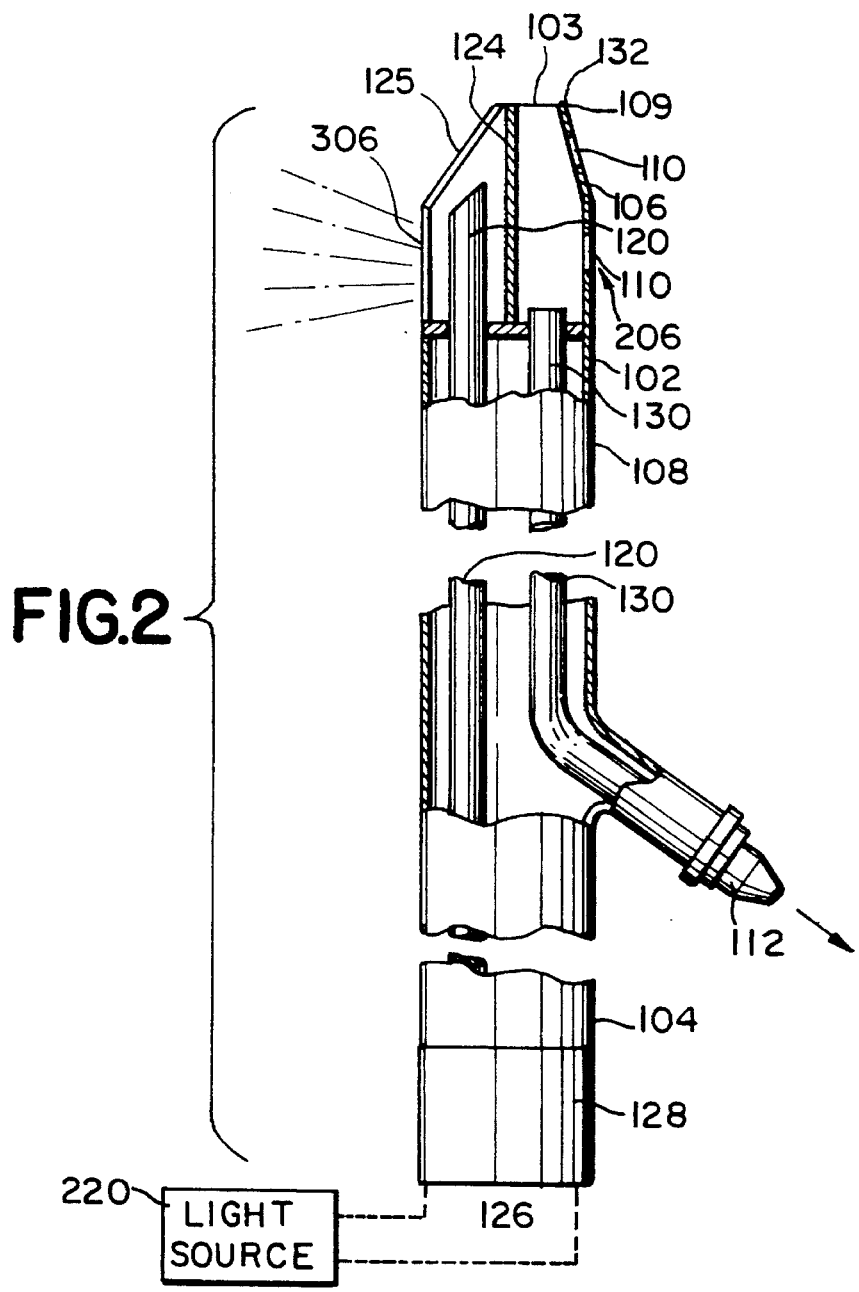
FIG. 2 is a partially broken-away plan view of an intracardiac illuminator made in accordance with the present invention

Referring now to FIG. 2, a partially broken away, enlarged view of the device shown in FIG. 1 is illustrated. As explained above, a fiber optic cable 120 runs inside this instrument from the tip 103 of cardiac end 102 to the light source end 104. This optic fiber 120 is preferably of about 2 mm (0.08 inches) in diameter and is also preferably hermetically sealed over its length by the tubing 108 to avoid entry of bacteria and moisture. As seen in FIG. 2, the aspiration tube 130 is disposed in the cardiac end 102 of the device 100. The aspiration tube 130 is preferably also comprised of silicone tubing and preferably has an internal diameter of 2 mm (0.08 inches). The distal (cardiac) end 132 of the aspiration tubing 130 connects to the housing 106 and is in fluid communication with the housing 106 and the outside environment. Thus, in a preferred embodiment, the housing 106 contains the last 1 cm (0.4 inches) of the aspiration tubing 130. FIG. 2 also illustrates the aspiration opening 109 and two side openings 110 that preferably have a diameter of 2 mm (0.08 inches) each that are provided in a preferred embodiment to admit fluid into the aspiration tubing 130. As explained above, the aspiration tubing 130 exits from the tubing 108 that provides a covering for the device 100 about 60 cm (23.6 inches) from the cardiac end 102 and terminates in a connector 112. The connector 112 most preferably is of the type adapted to be connected to a cardiotomy suction device during, for example, cardiopulmonary bypass.

Referring still to FIG. 2, in a preferred embodiment, the fiber optic cable 120 is covered by a thin glass shield or covering 125 to prevent exposure of the optical fibers that make up the cable 120 to moisture. In addition, the housing is most preferably constructed to provide or accept a reflector 124 to focus the light emitted from the distal tip 103 of the device. In a most preferred embodiment, the reflector 124 is about 2 mm (0.08 inches) in width and is optically connected to the distal tip of the fiber optic cable 130 to diffuse and focus the emitted light from the side wall of the device, into the area of interest. The proximal (light source) end 126 of the fiber optic cable 120 is terminated by a connector 128 that can be connected to any standard light source, as well known in the art.

In the preferred embodiment discussed above, the diameters of the cardiotomy suction conduit and fiber optic cable were chosen as 2 mm (0.08 inches), an appropriate size for children and small adults. It has been found, however, that a full-sized adult heart can accommodate a somewhat larger device that uses a fiber optic cable and aspiration tube of about 3 mm (0.12 inches) in diameter.

Referring now to FIG. 3, further details of the housing 106 that preferably forms the distal tip 103 of the device 100 are illustrated in the form of an alternate embodiment of the present invention. As shown in a perspective view, the housing 106 is sized and designed to physically accommodate both the aspiration tubing 130 and the fiber optic cable 120. Moreover, an aspiration section 206 is designed to provide an opening at the distal tip 103 as well as to provide lateral openings 110 as described above. As shown by the arrows on FIG. 3, these orifices create an efficient flow pattern and aspirate fluid from the site. Another section of the housing 106 is the illumination section 306, which contains the thin glass shield or lens 125 and the reflector 124 described above. Those of skill in the art will appreciate that the housing 106 itself can be machined or formed to provide a contour that will act as a reflector and focus or diffuse the light as desired. Alternatively, the housing can be formed to accept a reflector 124 as a separate component. Although it is preferred that the housing 106 be fabricated from surgical grade stainless steel, many acceptable plastic materials and other synthetic materials are known in the art that would provide sufficient structural integrity to accept the aspiration tubing and fiber optic cable and be compatible with the outer cover tubing 108. Additionally, although the shape of the housing 106 illustrated presents a preferred embodiment, those of skill in the art will realize that the housing 106 can be constructed using a variety of geometries while still achieving the same results. In particular, it will be observed that in order for a portion of the light to be transmitted sustantially radially, the fiber optic bundle is preferably light cut at an angle less than 90 degrees relative to its longitudinal dimension as shown. The reflector 124 will reflect light where it is not blocked by the fiber bundle, as seen in FIG. 2.

Figure 6:
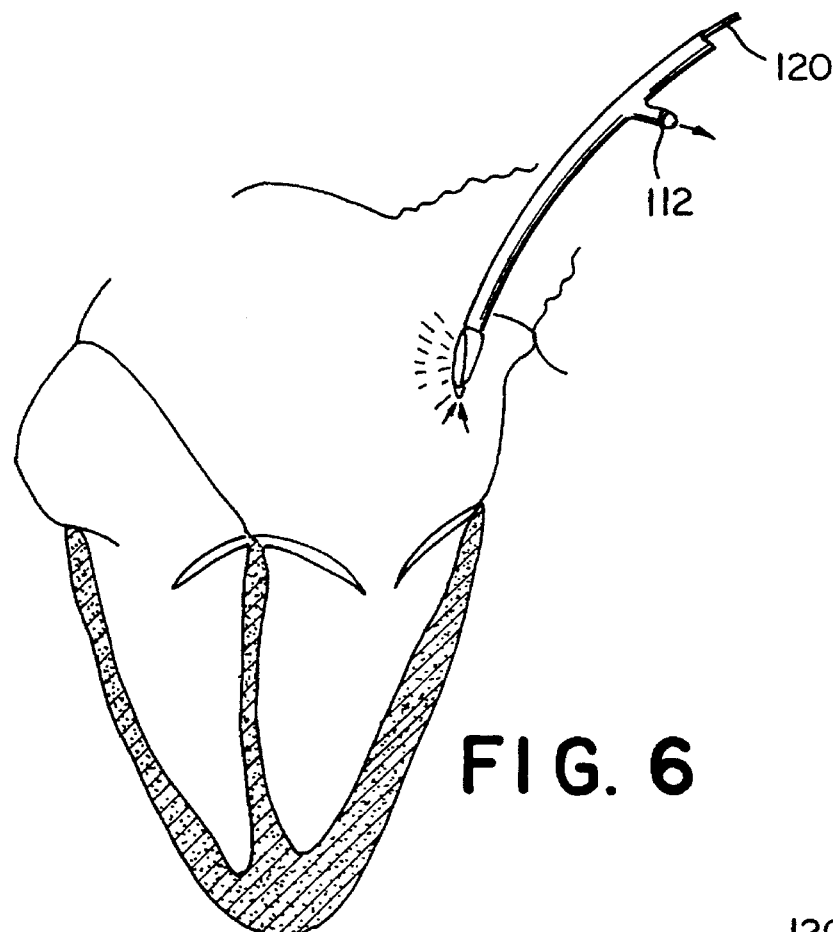
FIG. 6 shows the placement of the present invention within the left atrium during AV canal repair and mitral valve repair/replacement.
Figure 7:
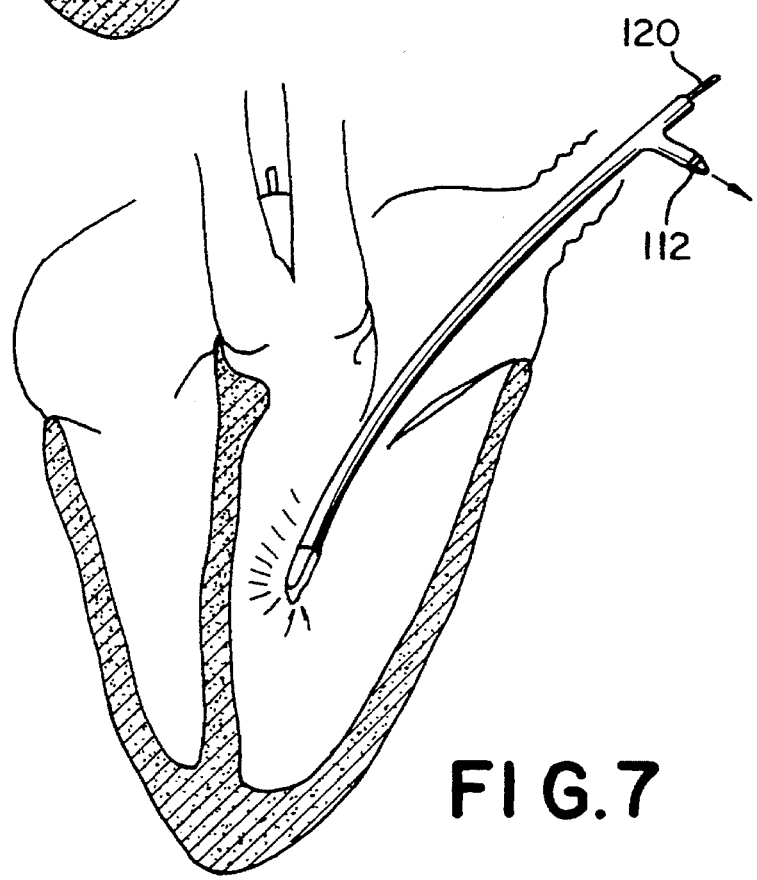
FIG. 7 is a view similar to FIG. 5, wherein the present invention is disposed within the left ventricle to illuminate the subaortic membrane.

An enlarged cross-section is illustrated in FIG. 4. As shown, the suction tip 108 has a cone-shaped screen 132 covering the opening of the suction tube 130. In a most preferred embodiment, the suction tip 108 is slightly longer than the portion of the housing 106 that includes the optical fiber 120. Another aspect of this preferred embodiment is that the housing 106 permits light to escape from the side of the device, as shown. A clear covering 125 protects and seals the fibers. Most preferably, a reflector 124 is disposed within the housing 106 between the optic fibers and the aspiration section 107 so that all the useful light is emitted as shown. Such a reflector 124 may be part of the housing 106 or may be affixed to the back of the fibers, e.g., a foil backing. Illustrations of this embodiment in use are shown in FIGS. 5–7. However, it will be understood that although FIGS. 5–7 illustrate the invention being used in different procedures, the invention is not to be limited to any particular use or embodiment.

The technique for using the present invention may be explained with reference to FIG. 5. One method of using the intracardiac illuminator device 100 of the present invention is by introducing the device 100 through an open right atrium (RA) across a patent foramen ovale or an atrial septal defect (if one is present) or by making a slit in the interatrial septum. The device 100 is then advanced into the left atrium (LA) and across the mitral valve (MV) into the left ventricle (LV). Once the distal end 102 is passed across the patent foramen ovale, the device can be pushed blindly into the left ventricle (LV) across the mitral valve (MV) in a technique similar to that used to insert a left ventricular vent. This technique should be the most common method of usage in congenital heart surgery where entry is most commonly through right atrium and right ventricle. Once the light guide (distal) end 102 enters the left ventricle, the cardiotomy suction channel can be connected to a cardiotomy suction device using the connector 112 described above. One benefit of the present invention is that the fiber optic cable 120 emits a relatively "cold" light transmitted from a remote light source 220, thus warming of the heart is essentially eliminated during bypass. Other places where the present invention can be placed are left atrium (LA), right ventricle (RV), right atrium (RA), pericardial cavity and pleural cavity.

One of the most common situations for the use of the present invention in intracardiac surgery is to close ventricular septal defects (VSD); this use is also shown in FIG. 5. All the margins of any type of ventricular septal defect can be brightly illuminated, as shown by the light rays in FIG. 5, including its relationship to the aortic valve through the right atrium or right ventricle. In use, the upper margin of the ventricular septal defect can be clearly seen. The upper margin is the most problematic of all to visualize because the headlights now used for illumination cannot focus on it; however, this is the site of the most common cause of residual ventricular septal defect.

The occurrence of multiple muscular ventricular septal defects is another situation where all small muscular ventricular septal defects can be seen using the present invention as they transmit light from the left ventricle across the ventricular septal defect. Usually, it is very difficult to locate these small muscular ventricular septal defects in the dark. However, using the present invention, the disappearance of all light in the right ventricle can be an indicator of closure of all ventricular septal defects.

The repair of a Tetralogy of Fallot condition is another situation where the present invention permits infundibular resection to be done very precisely, in good light, without injuring adjacent structures. A ventricular septal defect can be closed through the right atrium or the right ventricle with good visibility. As shown in FIG. 6, the device 100 can also be inserted through the subaortic membrane. Thus, the present invention is useful in an intraventricular surgery for congenital heart defects like the Rastelli operation, atrioventricular canal defect repair, infundibular PS resection, idiopathic hypertrophic subaortic stenosis (IHSS) repair, or similar procedures. In adult cardiac surgery, when the device 100 is placed in left ventricle, it is useful for aortic valve replacement, left ventricle aneurysm resection, arrthymia surgery on left ventricle (endocardial resections), the Konno operation, other aortic root enlargement procedures, intraventricular tumor resection, or similar procedures.

Referring now to FIG. 7, the device 100 of the present invention may also be placed in an open left atrium (LA) where its lighting and the cardiotomy suction effect are very useful in operations such as mitral valve replacement, repair, atrioventricular canal repair, the Senning operation, or similar procedures.

All types of surgery inside the right ventricle are also aided by the present invention, including Tetralogy of Fallot repair, DORV repair, the Rastelli operation, or similar procedures.

Finally, when placed inside the pericardial cavity, the present invention illuminates and clears the field of all blood without the need for holding an aspiration device in hand by providing illumination for surgery on the base of the heart like coronary artery bypass grafts to obtuse marginal branches, posterior descending branches, or the like.

To summarize, the intracardiac illuminator of the present invention can be useful in any type of surgery inside the heart, pericardial cavity or even the pleural cavity. It eliminates the need for using a headlight which, among other disadvantages, can touch the sterile field while working at awkward angles. It provides excellent illumination to any place where a headlight cannot reach and might even replace a headlight completely.

Although certain embodiments of the present invention have been disclosed herein and described with particularity, these description are for purposes of illustrating and explaining the present invention and are not limiting. Upon review of the foregoing description, those of skill in the art will realize that there are numerous adaptations, modifications and variations that are readily made which are still within the spirit of the present invention while departing from the specific embodiments disclosed. Accordingly, reference should be made to the appended claims in order to ascertain the full scope of the present invention.

What is claimed is:

1. A flexible illumination and suction device comprising a flexible fiber optic cable having a distal end terminated directly below a transparent cover that forms part of a first section of a rigid, two section housing having a length that is a minor portion of the cable, and a proximal end connected to a light source disposed outside the device; a single flexible aspiration conduit having a distal end connected to and in fluid communication with an opening providing fluid communication with a second section of the rigid housing to create a single aspiration channel and a proximal end terminated by a suction connector; and a flexible tubular body surrounding the fiber optic cable and the aspiration conduit therein and sealed to the housing and the connector in a fluid tight manner, wherein the fiber optic cable comprises a bundle of fibers cut at an angle of less than 90 degrees relative to its longitudinal dimension and thereby directly emits light in a radial direction from the fibers of the bundle, and wherein the second section of the housing terminates in an aspiration tip disposed distally forward of the first section, whereby fluid is rapidly aspirated to permit an area of tissue to be observed.

2. The apparatus of claim 1, wherein the housing comprises a reflector for directing light emitted by the fiber optic cable.

3. The apparatus of claim 2, wherein the reflector is an integral portion of the housing.

4. The apparatus of claim 1, wherein the transparent cover is spaced apart from and protects the distal end of the fiber optic cable.

5. The apparatus of claim 1, wherein the fiber optic cable has a diameter between 2–3 millimeters (0.08–0.12 inches).

6. The apparatus of claim 1, wherein the second section comprises at least one opening formed in a sidewall of the housing.

7. The apparatus of claim 6, wherein the fiber optic cable has a first length and the aspiration conduit has a second length that is less than the first length.

8. The apparatus of claim 7, wherein the first length is about 180 cm (70.9 inches) and the second length is about 60 cm (23.6 inches).

9. The apparatus of claim 1, wherein the second section comprises a conical aspiration tip comprising a plurality of openings for admitting fluid into the aspiration conduit.

10. The apparatus of claim 1 wherein the aspiration conduit is comprised of silicone tubing.

11. The apparatus of claim 1, wherein the inner diameter of the aspiration conduit is about 2 mm (0.08 inches).

12. The apparatus of claim 1, wherein the tubular body is comprised of silicone tubing.

13. A flexible intracardiac illumination and aspiration device for insertion within a heart comprising:

a flexible fiber optic cable having a distal end, a proximal end, and a first length, wherein the proximal end is connected to a light source disposed outside the device and the distal end comprises a bundle of fibers cut at an angle of less than 90 degrees relative to its longitudinal dimension and thereby directly emits light in a radial direction from the cable;

a single flexible aspiration conduit having a distal end, a proximal end and a second length, wherein the proximal end is terminated by a connector adapted to connect the aspiration conduit to a cardiotomy suction source;

a rigid housing connected to the distal end of the fiber optic cable that is a minor portion of the length of the cable and comprising a first section for receiving the distal end of the fiber optic cable comprising a transparent cover portion for permitting emitted light to exit in a radial direction, the housing further comprising a second section that terminates in an aspiration tip disposed distally forward of the first section, the aspiration tip comprising an opening connected to and in fluid communication with the aspiration conduit; and a flexible tubular body, having a cross-section, surrounding the fiber optic cable and the aspiration conduit therein and sealed to the housing and the connector in a fluid-tight manner, whereby fluid is rapidly aspirated to permit an area of tissue to be observed.

14. The intracardiac device of claim 13, wherein the first length is greater than the second length.

15. The intracardiac device of claim 14, wherein the first length is about 180 cm (70.9 inches) and the second length is about 60 cm (23.6 inches).

16. The intracardiac device of claim 13, wherein the diameter of the fiber optic cable and the inner diameter of the aspiration conduit are both about 2–3 mm (0.08–0.12 inches).

\* \* \* \* \*